United States Patent
Abels et al.

(10) Patent No.: US 7,458,811 B2
(45) Date of Patent: *Dec. 2, 2008

(54) KITS COMPRISING A PLURALITY OF BITE RAMPS HAVING DIFFERENT ANGLES FOR ORTHODONTIC TREATMENT

(76) Inventors: Norbert Abels, Alleestrasse 30a, 66424 Homburg (DE); Claus-H. Backes, St. Wendeler Strasse 45, 66113 Saarbrücken (DE)

( * ) Notice: Subject to any disclaimer, the term of this patent is extended or adjusted under 35 U.S.C. 154(b) by 163 days.

This patent is subject to a terminal disclaimer.

(21) Appl. No.: 11/560,306

(22) Filed: Nov. 15, 2006

(65) Prior Publication Data

US 2007/0111153 A1 May 17, 2007

Related U.S. Application Data

(63) Continuation of application No. 11/232,694, filed on Sep. 22, 2005, now Pat. No. 7,226,287, which is a continuation-in-part of application No. 10/835,963, filed on Apr. 30, 2004, now Pat. No. 7,293,987, which is a continuation-in-part of application No. 10/837,477, filed on Apr. 30, 2004, now abandoned.

(51) Int. Cl.
*A61C 3/00* (2006.01)

(52) U.S. Cl. .......................... 433/18; 433/19
(58) Field of Classification Search .............. 433/18, 433/19, 21, 22, 180
See application file for complete search history.

(56) References Cited

U.S. PATENT DOCUMENTS

| 3,797,114 | A | | 3/1974 | Wiland |
| 4,256,456 | A | * | 3/1981 | Wallshein .................... 433/21 |
| 4,439,149 | A | | 3/1984 | Devincenzo |
| 4,509,918 | A | | 4/1985 | Clark |
| 4,619,609 | A | | 10/1986 | Clark |
| 4,773,857 | A | * | 9/1988 | Herrin ......................... 433/138 |
| 4,793,803 | A | | 12/1988 | Martz |
| 4,834,656 | A | | 5/1989 | Loudon |
| 4,880,380 | A | | 11/1989 | Martz |
| 5,078,596 | A | | 1/1992 | Carberry et al. |

(Continued)

OTHER PUBLICATIONS

Office Action dated Dec. 13, 2005 cited in related U.S. Appl. No. 10/835,963.

(Continued)

*Primary Examiner*—Kenneth Bomberg
*Assistant Examiner*—Matthew M Nelson
(74) *Attorney, Agent, or Firm*—Workman Nydegger (57) ABSTRACT

A bite ramp includes a tooth-attachment element and ramp element. The tooth-attachment element is sized and configured for bonding to the lingual surface of a person's tooth, while the ramp element may be either fixed or else hingedly or bendably adjustable relative to the tooth-attachment element. The ramp element provides a ramp at a desired angle for engaging a corresponding tooth of the opposite dental arch when the person's mouth is closed. The engagement between the ramp element and the corresponding tooth of the opposite dental arch may cause the lower jaw to move forward, rearwardly, or not at all relative to the upper jaw, thereby incrementally correcting a deep bite or other abnormal orthodontic condition. A kit may be provided that includes multiple bite ramps, at least two of which initially include different ramp angles.

13 Claims, 10 Drawing Sheets

U.S. PATENT DOCUMENTS

| | | | |
|---|---|---|---|
| 5,145,364 | A | 9/1992 | Martz et al. |
| 5,443,384 | A | 8/1995 | Franseen et al. |
| 5,678,991 | A | 10/1997 | Eganhouse |
| 5,697,780 | A * | 12/1997 | Tuneberg et al. ............... 433/9 |
| 5,846,074 | A | 12/1998 | Klapper |
| 5,871,350 | A | 2/1999 | Clark et al. |
| 6,027,340 | A | 2/2000 | Chun |
| 6,053,729 | A | 4/2000 | Brehm et al. |
| 6,099,304 | A | 8/2000 | Carter |
| 6,932,598 | B1 | 8/2005 | Anderson |
| 7,001,180 | B2 | 2/2006 | Bass |
| 7,018,203 | B2 | 3/2006 | Clark |
| 2002/0025502 | A1 | 2/2002 | Williams |
| 2002/0182559 | A1 | 12/2002 | Kamisugi |
| 2003/0031976 | A1 | 2/2003 | Clark |
| 2003/0124479 | A1 | 7/2003 | Bass |
| 2005/0244778 | A1 | 11/2005 | Abels et al. |
| 2005/0244779 | A1 | 11/2005 | Abels et al. |
| 2006/0008761 | A1 * | 1/2006 | Allred ........................... 433/9 |
| 2006/0014117 | A1 | 1/2006 | Abels et al. |

OTHER PUBLICATIONS

Office Action dated Jun. 14, 2006 cited in related U.S. Appl. No. 10/835,963.

Office Action dated Feb. 21, 2007 cited in related U.S. Appl. No. 10/835,963.

Notice of Allowance dated Jul. 26, 2007 cited in related U.S. Appl. No. 10/835,963.

Supplemental Notice of Allowability dated Sep. 12, 2007 cited in related U.S. Appl. No. 10/835,963.

Office Action dated Dec. 13, 2005 cited in related U.S. Appl. No. 10/837,477.

Office Action dated Mar. 9, 2006 cited in related U.S. Appl. No. 11/232,694.

Office Action dated Jun. 14, 2006 cited in related U.S. Appl. No. 11/232,694.

Notice of Allowance dated Dec. 6, 2006 cited in related U.S. Appl. No. 11/232,694.

Office Action dated Sep. 17, 2007 cited in related U.S. Appl. No. 11/553,909.

Office Action dated Mar. 4, 2008 cited in related U.S. Appl. No. 11/553,909.

Office Action dated Jul. 14, 2008 cited in related U.S. Appl. No. 11/553,909.

* cited by examiner

Fig. 8

KITS COMPRISING A PLURALITY OF BITE RAMPS HAVING DIFFERENT ANGLES FOR ORTHODONTIC TREATMENT

RELATED APPLICATIONS

The present application is a continuation of U.S. patent application Ser. No. 11/232,694, filed 22 Sep. 2005 and titled "Kits Comprising a Plurality of Bite Ramps Having Different Angles for Orthodontic Treatment", which is a continuation-in-part of U.S. patent application Ser. No. 10/835,963, filed Apr. 30, 2004 and titled "Adjustable bite ramps for deep bite correction and kits incorporating bite ramps," and U.S. patent application Ser. No. 10/837,477, filed Apr. 30, 2004 and titled "Method of Correcting a Deep Bite Condition Using Adjustable Bite Ramps," each of which is hereby incorporated by reference in its entirety.

BACKGROUND OF THE INVENTION

1. The Field of the Invention

The present invention is in the field of orthodontics, more particularly to apparatus and methods for the correction of a variety of orthodontic conditions, including, e.g. class II malocclusions, class III malocclusions, and/or "deep bite," also known as "overbite".

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth or the jaw to correct underbites or overbites. For example, orthodontic treatment can improve the patient's occlusion, or enhanced spatial matching of corresponding teeth.

A Class II malocclusion occurs when the first molar of the lower dental arch is distal relative to the first molar of the upper dental arch. Class II malocclusions often also result in a condition where the upper incisors are positioned excessively anterior (e.g., more than about 1 mm) of the lower incisors when the teeth are occluded. This condition is often referred to as "overjet".

A Class III malocclusion occurs when the first molar of the lower dental arch is anterior relative to the first molar of the upper dental arch. A Class III malocclusion can result in a condition where the lower incisors are positioned anterior of the upper incisors when the teeth are occluded. This condition is sometimes referred to as a "negative overjet".

Overbite, also known as "deep bite," occurs when there is excessive vertical overlap of the incisors. Any of these conditions can result in increased wear of the incisors or other teeth, periodontal problems, increasingly visible gum tissue, and increased instances of the patient biting the roof of their mouth or other soft tissues. In addition, correction of such conditions often results in a more aesthetically appealing smile for the patient.

Depending on the severity of the condition, correction can sometimes be achieved with installation and use of dental braces and/or bite openers and elastics, although orthognathic surgery is sometimes required. Installation of dental braces can be ineffective in effecting sufficient movement of the jaw, existing bite openers and elastics are often intrusive, complex, and uncomfortable, and orthognathic surgery is expensive, invasive, and uncomfortable, especially from a patient's perspective.

Therefore, there exists a need for devices and kits that can be used to provide less expensive, simpler, less invasive orthodontic correction.

BRIEF SUMMARY OF THE PREFFERED EMBODIMENTS

The bite ramps of the present invention include a tooth-attachment element and a ramp element. The tooth-attachment element is sized and configured for bonding to the lingual surface of a person's tooth (e.g., an upper or lower incisor and/or canine), while the ramp element is either fixed or hingedly or bendably adjustable relative to the tooth-attachment element.

The ramp element provides a ramp structure at a desired angle for engaging the corresponding teeth of the opposite dental arch (e.g., the upper or lower incisors and/or canines) when the person's mouth is closed. In one embodiment, the engagement between the ramp structure and the corresponding teeth of the opposite dental arch causes the lower jaw to move forward relative to the upper jaw, while also disoccluding the lateral teeth and allowing a new neutral occlusion. The bite ramps may also be used in combination with class II elastics to assist in moving the lower jaw forward. In other embodiments, the ramp structure may be angled so as to prop open the jaw in a desired manner without moving the jaw, or even move the lower jaw rearwardly relative to the upper jaw.

The bite ramps according to one embodiment are adjustable and may be made from metal, plastic, or another somewhat flexible material so as to allow adjustment of the ramp element. Suitable metals include stainless steel, titanium, and titanium alloys. Preferably, any metals used are nickel free or have a low nickel content so as to avoid patient sensitivity which can sometimes be caused by nickel. According to one embodiment, the adjustable ramps may be injection molded from a plastic.

The adjustable bite ramps may further comprise means for locking the ramp element in a desired adjustment angle relative to the tooth-attachment element. An example of such a means for locking is a curable resin that is applied to and cured between the tooth-attachment and ramp elements. The cured resin locks the ramp element in a desired adjustment angle, and provides a more comfortable surface for the patient's tongue and soft tissues.

According to another embodiment, an optional shoe may be placed over the bite ramp. The shoe may be bonded to the bite ramp with an adhesive. In use, the lower surface of the shoe provides the ramp for engaging the corresponding tooth of the opposite dental arch. The upper surface provides a smoother surface within the patient's mouth (e.g., to provide enhanced comfort and/or to help prevent buildup of plaque or other foreign matter).

An exemplary method of use involves providing one or more adjustable bite ramps, bonding the bite ramps to the lingual surface of one or more of a person's top teeth (e.g. the front incisors), adjusting the bite ramps to provide a ramp structure at a desired angle for engagement with the corresponding teeth of the opposite dental arch (e.g. the lower incisors) when the mouth is closed, and locking the ramp element in the desired adjustment angle. According to one embodiment, the ramp angle is selected so that the engagement between the ramp element and the teeth of the opposite dental arch pulls the lower jaw forward, closing and correcting the "deep bite" condition. In other embodiments, the lower jaw may remain stationary or it may move rearwardly.

According to an alternative embodiment, the bite ramps may be provided in a kit comprising a plurality of bite ramps, which may be adjustable or fixed, having a plurality of preselected angles. A fixed bite ramp includes a tooth-attachment element, a ramp element attached to the tooth-attachment element so as to provide a ramp structure at a fixed angle for engagement with a corresponding tooth of the opposite dental arch upon closing the patient's mouth. In the case where the kit includes adjustable bite ramps, it may also advantageously include means for locking the ramp element at a fixed angle relative to the tooth-attachment element. An exemplary kit of bite ramps may include a first fixed bite ramp having a ramp structure at a first fixed angle (e.g., an acute angle) and a second fixed bite ramp having a ramp structure at a second fixed angle (e.g., an obtuse angle, a different acute angle, or a right angle) that is different from the first fixed angle. In one kit, the included bite ramps may include ramp elements of different lengths.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The bite ramps of the present invention include a tooth-attachment element and a ramp element. The tooth-attachment element is sized and configured for bonding to the lingual surface of a person's tooth (e.g., an upper incisor), while the ramp element is either fixed or hingedly or bendably adjustable relative to the tooth-attachment element. The ramp element provides a ramp structure at a desired angle for engaging the corresponding tooth of the opposite dental arch (e.g., the lower incisor) when the person's mouth is closed. The engagement between the ramp and the corresponding teeth of the opposite dental arch props the lower jaw open relative to the upper jaw. Depending on the ramp angle, the bite ramp may cause the lower jaw to move forward relative to the upper jaw, remain stationary, or even move rearwardly relative to the upper jaw. In some cases, movement of the lower jaw may be assisted by the use of class II elastics attached to, e.g., the lower end molars and the upper canines.

II. Exemplary Adjustable Bite Ramps

Figure 1A:
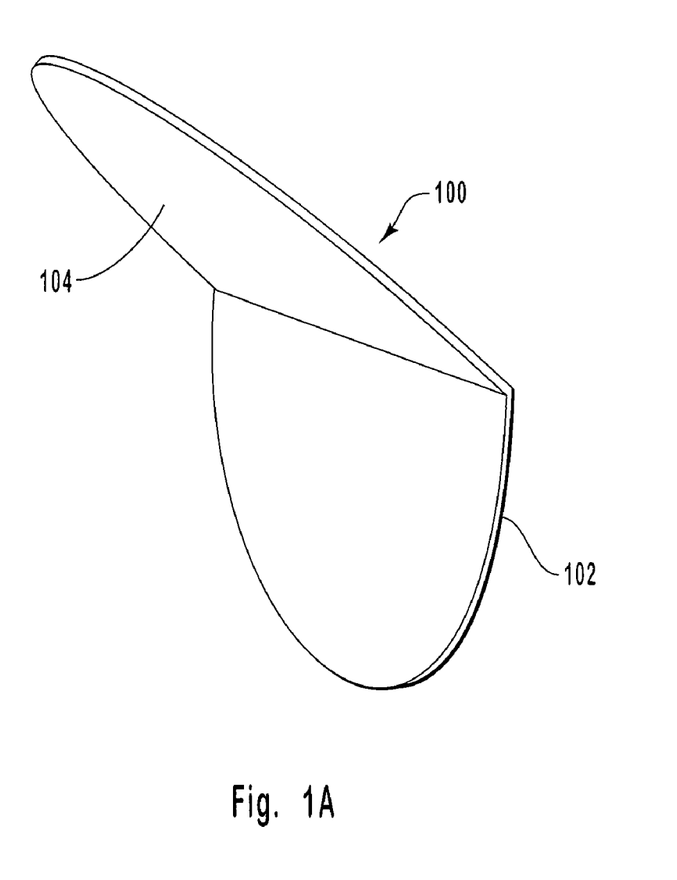
FIG. 1A is a perspective view of an exemplary adjustable bite ramp according to the invention.

FIG. 1A illustrates an exemplary adjustable bite ramp 100. The adjustable bite ramp 100 includes a tooth-attachment element 102 and a ramp element 104. The tooth-attachment element 102 is configured for bonding to the lingual surface of a person's front tooth (e.g., one or more upper or lower incisors and/or canines). In the illustrated embodiment, the ramp element 104 is bendably adjustable relative to the tooth-attachment element 102. The adjustability of the ramp element 104 provides a ramp structure at a desired angle for engaging the corresponding tooth of the opposite dental arch upon closing the person's mouth.

The adjustable bite ramps 100 may be made from metal, plastic, or another suitable material (e.g., a strip crown) so as to allow adjustment of the ramp structure. Suitable metals include stainless steel, titanium, and titanium alloys. Preferably, any metals used are substantially nickel free or have a low nickel content so as to avoid patient sensitivity which can sometimes be caused by nickel. According to one embodiment, the adjustable ramps may be injection molded from a plastic. Use of a transparent or translucent plastic material may be advantageous as it allows a light curable resin to be cured through the plastic material. The plastic material may be rigid or soft. Examples of some suitable plastic materials include ethyl vinyl acetate (EVA), polyvinyl chloride (PVC), polycarbonates, and silicone.

Figure 1B:
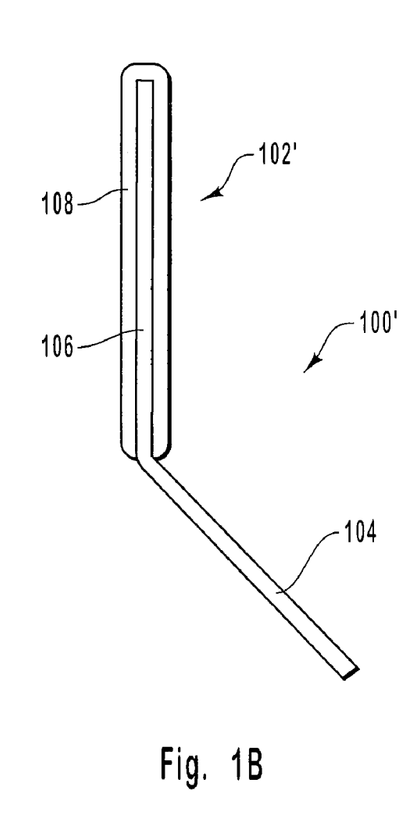
FIG. 1B is a perspective view of an alternative adjustable bite ramp according to the invention.

FIG. 1B illustrates an alternative embodiment of an adjustable bite ramp 100'. Adjustable bite ramp 100' includes a tooth-attachment element 102' and a ramp element 104. The tooth-attachment element 102 comprises an underlying support structure 106 that is integrally attached to the ramp element 104 and that further includes a polymer cover 108 that is overmolded over at least a portion of the support structure 106. The support structure 106 may include holes or perforations (not shown) that aid in mechanically interconnecting the overmolded polymer cover 108 over the support structure 106. One purpose of the polymer cover 108 is to provide a bonding surface that is more chemically compatible with adhesive bonding agents that may be used to adhere the tooth-attachment element 102' to a person's tooth during use. In addition, it provides a more comfortable surface for the soft tissues and the tongue when installed. The polymer cover 108' may optionally include undercuts (not shown) in order to promote better interaction and bonding between the polymer cover 108 and an adhesive. According to one embodiment, the polymer cover 108' may be curved to match the curvature of the lingual surface of an upper incisor (or other tooth).

III. Exemplary Method of Use

Figure 2A:
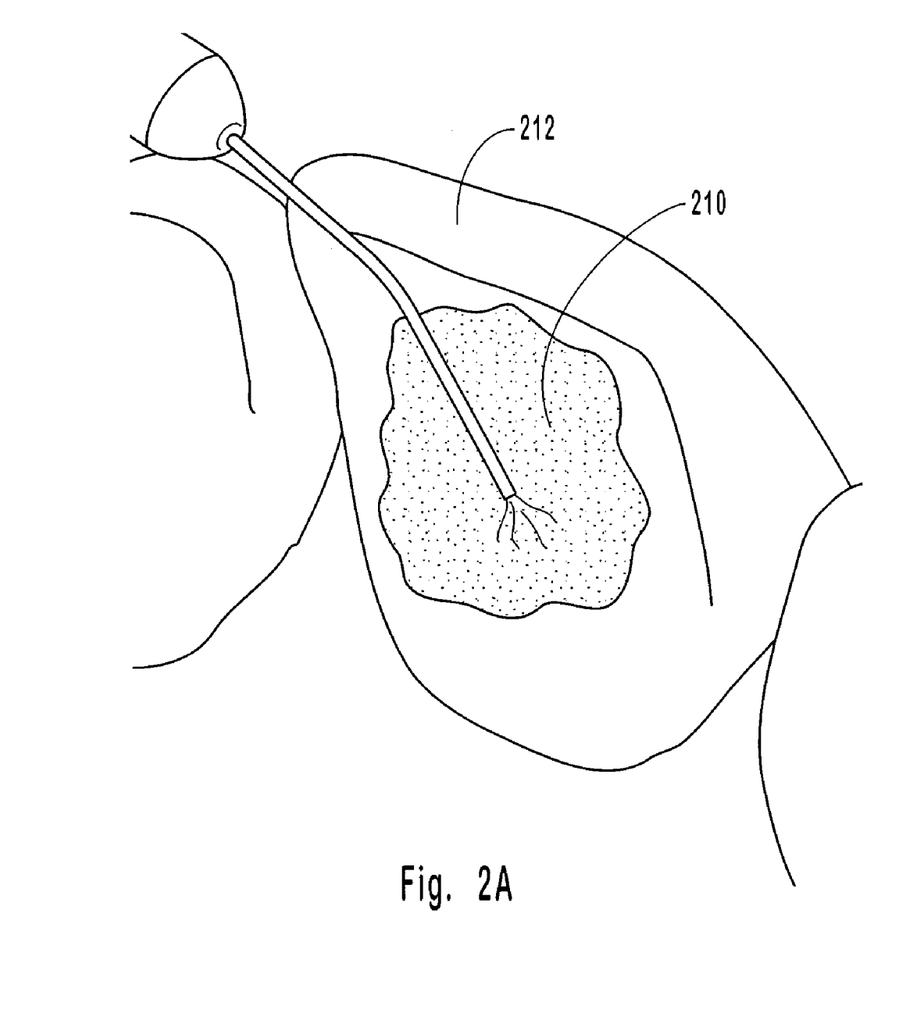
FIGS. 2A-2E depict installation of an adjustable bite ramp.
Figure 2B:
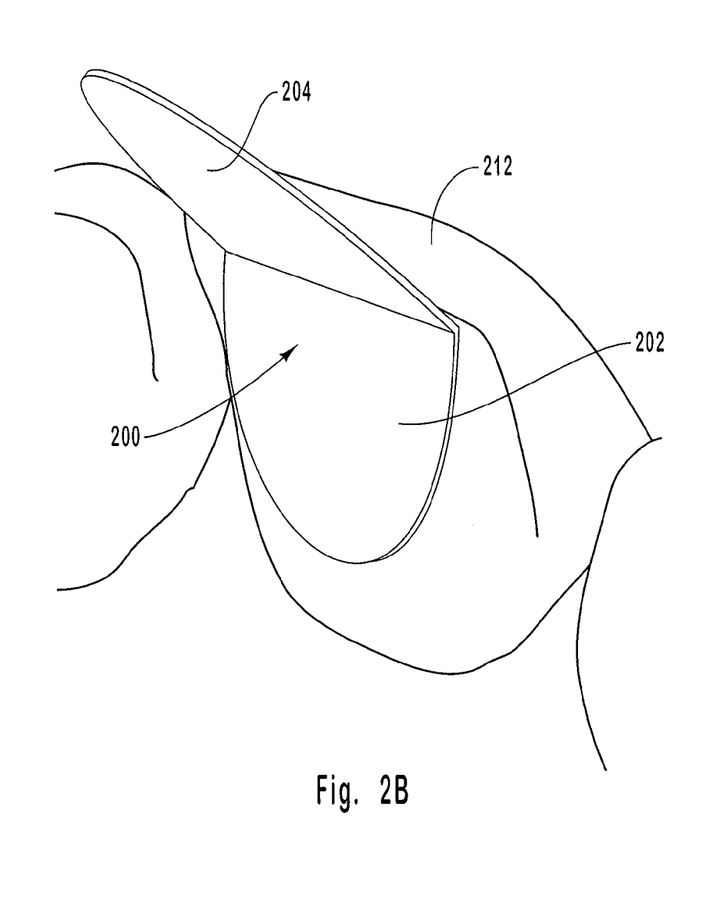

FIGS. 2A-2E illustrate an exemplary method of attaching the adjustable bite ramp 200 to a tooth. FIG. 2A shows an adhesive 210 being applied to the lingual surface of an upper incisor 212. The tooth-attachment element 202 of an adjustable bite ramp 200 is then positioned as desired on the lingual surface of incisor 212, as illustrated in FIG. 2B. Adhesive 210 may be any light or chemically curable adhesive resin known in the art of dentistry to adhere an appliance to a tooth.

Figure 2C:
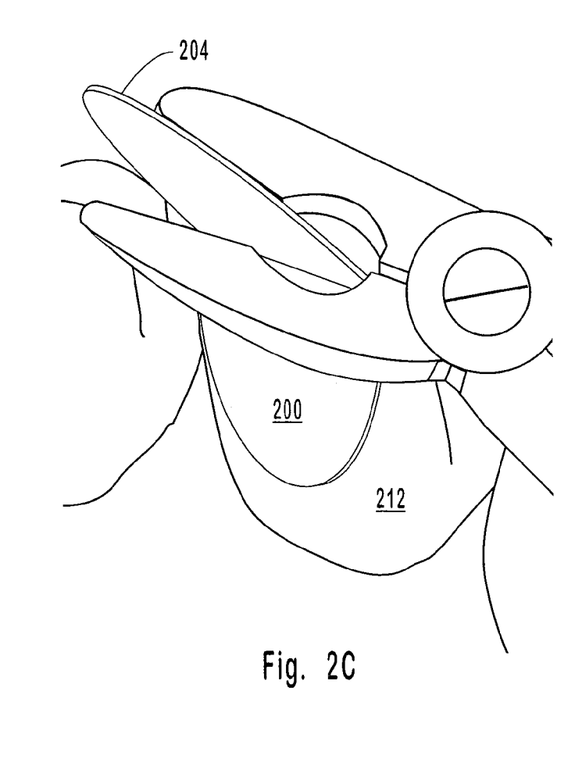

The ramp element 204 of adjustable bite ramp 200 is then adjusted (e.g., by bending) to provide a ramp structure at a desired angle, as illustrated in FIG. 2C. Any suitable tool for adjusting the ramp angle may be used (e.g., pliers, probes, or even a finger).

Figure 2D:
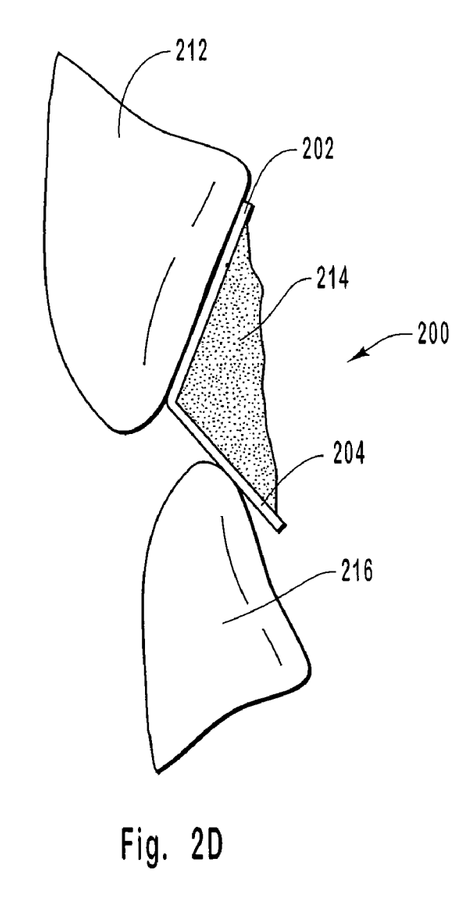
Figure 2E:
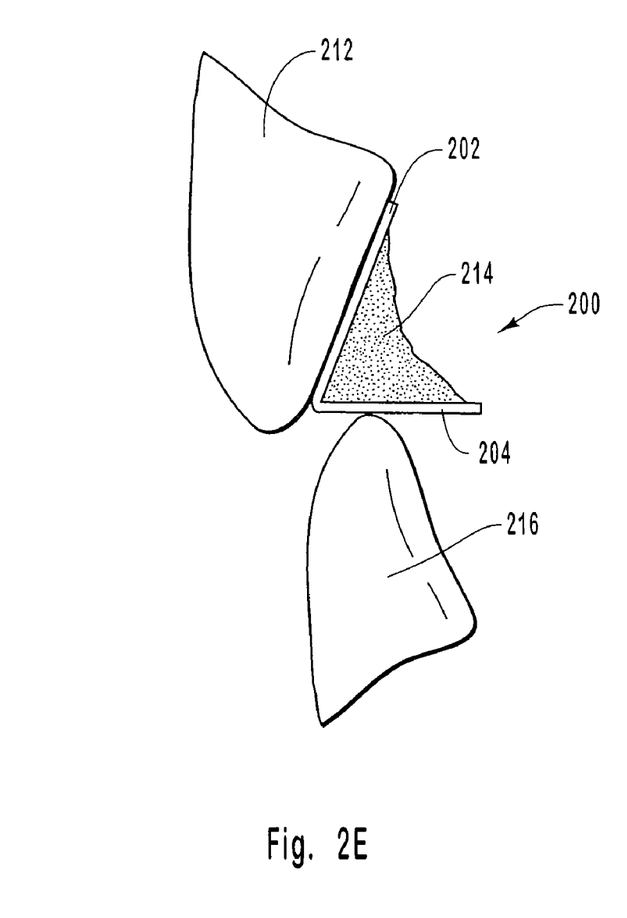

Once the ramp element 204 has been adjusted as desired, the area between the tooth-attachment element 202 and ramp element 204 of adjustable bite ramp 200 may be filled with a light or chemically curable composition 214 (e.g., a filled composite resin used to fill teeth or a luting cement). The composition 214 is cured and hardened so as to lock the ramp element 204 in the desired adjustment angle relative to tooth-attachment element 202, as illustrated in FIG. 2D-2E. Such a curable composition 214 is an example of means for locking a ramp element in a desired adjustment angle relative to a tooth-attachment element. If desired, a translucent or transparent form (e.g., of silicone) may be used when filling the gap between the tooth-attachment element 202 and the ramp element 204. The form holds the uncured resin in place during curing. The transparency or translucency of the form allows curing of the resin through the form.

FIG. 2D also illustrates how the adjustable bite ramp 200, more particularly the ramp element 204, engages the lower incisor 216 as the person's mouth is closed. The engagement between the ramp element 204 and the lower incisor 216 applies a force causing a person's lower jaw to move forward relative to the upper jaw. Although described as placed and acting on the incisors, it is to be understood that the bite ramps may be placed on any teeth needed according to the treatment desired (e.g., the bite ramps may be useful in the treatment of temporomandibular joint (TMJ) disorders).

The ramp element 204 of adjustable bite ramp 200 may be adjusted to provide a ramp structure at any desired angle. FIG. 2D illustrates the ramp element 204 having been adjusted so as to provide an oblique angle between the tooth-attachment element 202 and the ramp element 204. FIG. 2E alternatively illustrates a ramp element 204 having been adjusted so as to provide an acute angle between the tooth-attachment element 202 and the ramp element 204. The exact angle between the ramp element 204 and tooth-attachment element 202 may be selected depending on one or more of the relative positions of the upper and lower jaws, size of the person's teeth, angle of the teeth, desired degree of correction, and the like.

Figure 3A:
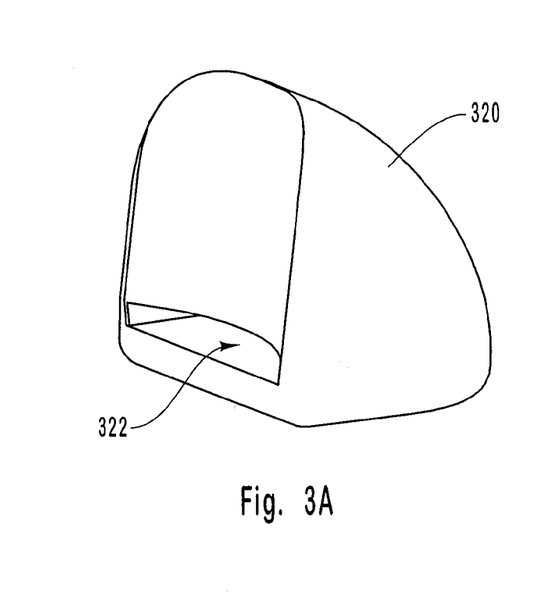
FIGS. 3A and 3B depict an optional shoe that may be used in association with an adjustable bite ramp.
Figure 3B:
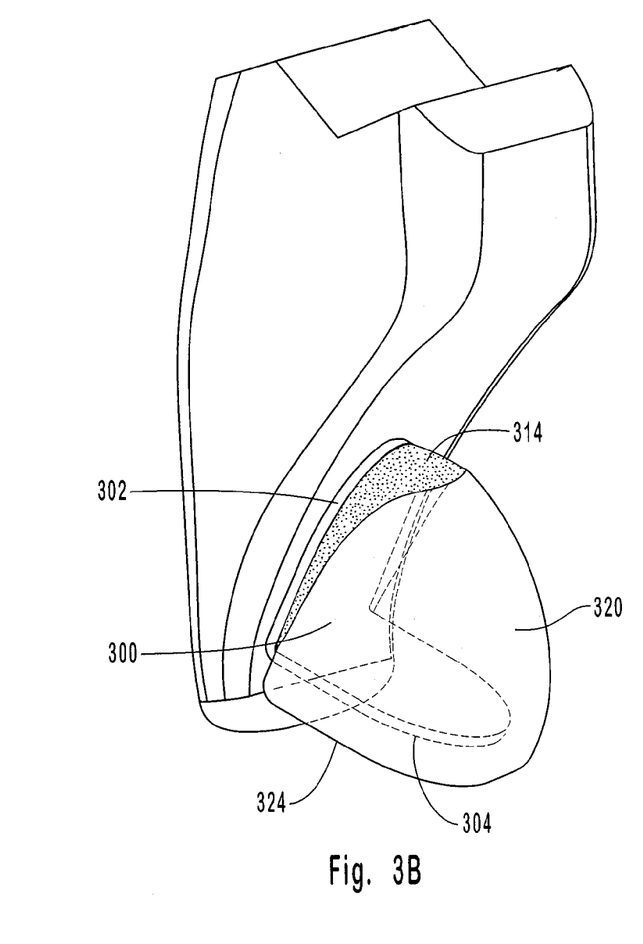

The adjustable bite ramps of the invention may optionally be used in combination with a shoe. FIGS. 3A and 3B illustrate an optional shoe 320 for use with an adjustable bite ramp 300. The shoe 320 may be placed over the ramp element 304 of bite ramp 300, more particularly by inserting ramp element 304 into a receiving slot 322 in the shoe 320. The shoe 320 may be bonded to the adjustable bite ramp 300 by use of an adhesive. When used, a lower surface 324 of the shoe 320 provides a ramp surface for slidable engagement with the corresponding tooth of the opposite dental arch (e.g., the lower incisor). As illustrated, the upper surface of the shoe 320 may be rounded so as to provide a smooth surface for increased patient comfort and/or to prevent build-up of plaque or debris.

The shoe 320 may be adapted to form a flush fit against the person's incisor, more particularly, the tooth-attachment structure 302 of the bite ramp 300. After adjustment of the ramp element 304, a space may exist between the shoe 320 and the tooth-attachment element 302, which is advantageously filled with a curable composition 314.

Figure 4A:
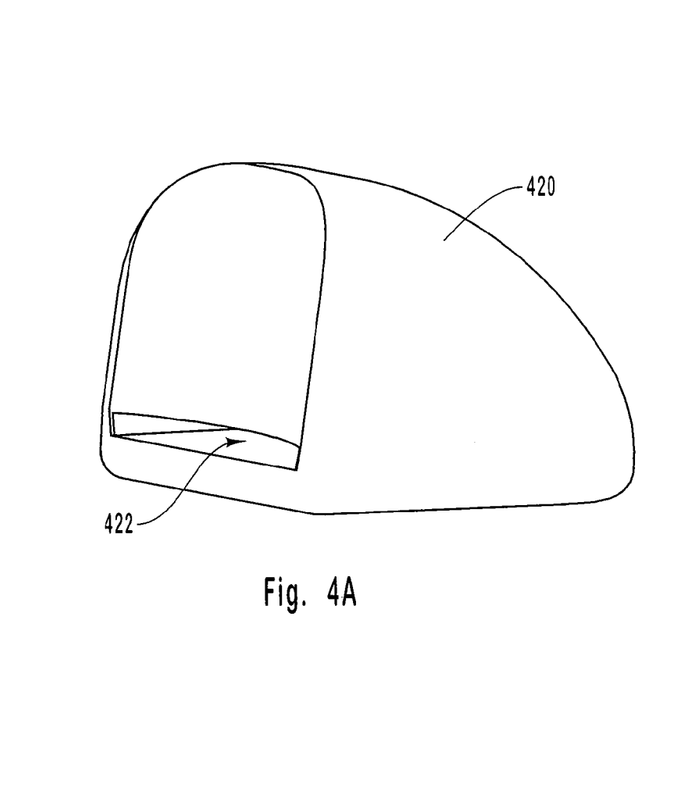
FIGS. 4A and 4B depict an alternative optional shoe that may be used in association with an adjustable bite ramp.
Figure 4B:
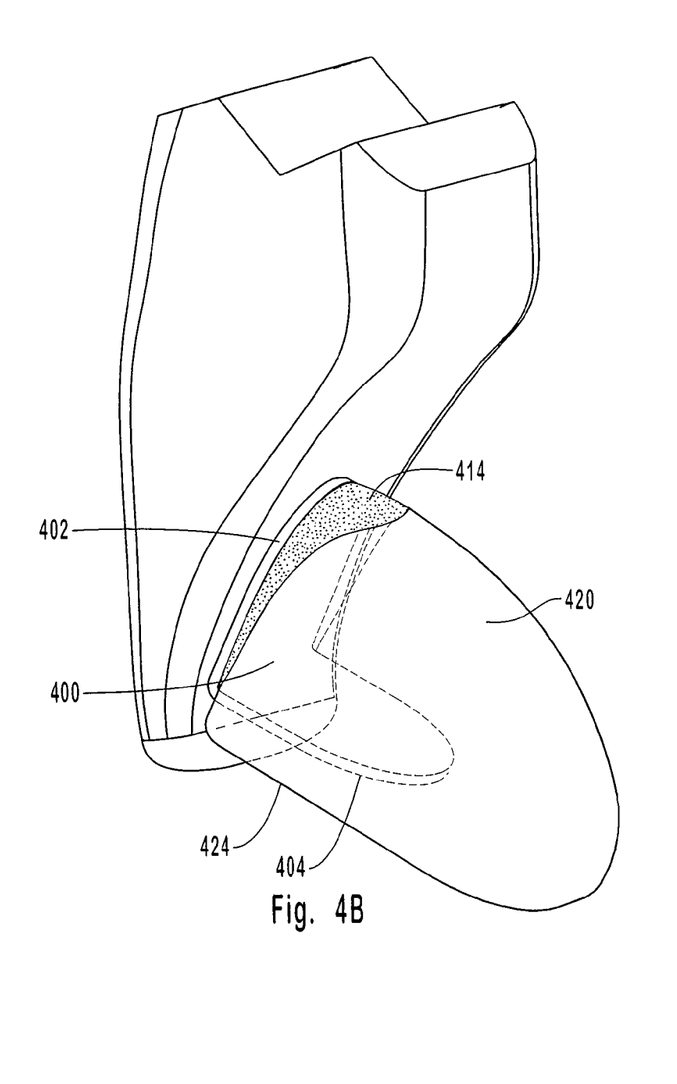

FIGS. 4A and 4B illustrate an alternative embodiment of a shoe 420 that is used in the same manner as shoe 320 illustrated in FIGS. 3A and 3B, except that the lower surface 424 of the shoe 420 is significantly longer than surface 324 of shoe 320. Providing an increased working length of the lower surface 424 may be desirable for treating more severe class II malocclusions.

During treatment, it may be desirable to begin treatment with a longer shoe 420 such as that illustrated in FIGS. 4A-4B. According to one embodiment, the shoe may be formed of a material (e.g., PEEK polyarylether ketone) that will form a weaker bond with the resin 414 used to fill space between the shoe 420 and tooth-attachment element 402 as compared to the bond between the tooth-attachment element 402 or an optional overmolded polymer cover (see FIG. 1B) (e.g., formed of a polymer such as TROGAMID nylon) and the filling resin 414. Using such a material allows preferential separation of the shoe 420 from the filling resin 414. As treatment progresses, the lower jaw is pulled forward. Once the lower jaw has been pulled sufficiently forward, the longer shoe 420 may be removed and replaced with a shorter shoe, such as shoe 320 illustrated in FIG. 3A-3B, which is less intrusive within the mouth of the patient.

Alternatively, treatment may begin with a longer shoe, such as that illustrated in FIGS. 4A-4B, and once the lower jaw has been pulled sufficiently forward, the end of the shoe may be ground or cut so as to form a shoe of a shorter length, which is less intrusive within the mouth of the patient. In addition, the shorter adjustable bite ramp may be used to stabilize an opened bite that has been achieved by earlier treatment. Temporarily continuing use of such a bite ramp prevents the treated teeth from returning to their original untreated configuration.

The bite ramps according to the invention may optionally be used in combination with class II elastics to move the lower jaw in a desired manner (e.g. forward). According to one method, respective elastics are stretched between the lower end molars and the upper canines.

According to another embodiment, bite ramps according to the invention may include a magnet for interacting with another magnet which may be attached to a corresponding tooth of the opposite dental arch. The magnets can be used to force the teeth apart and/or apply a force to move the teeth as desired (e.g. to intrude a tooth).

IV. Kits Comprising a Plurality of Bite Ramps

In addition to providing adjustable bite ramps, the present invention also contemplates kits that include a plurality of bite ramps, each having a pre-selected angle. The bite ramps may be adjustable or fixed. A kit of fixed bite ramps may include a first fixed bite ramp having a ramp structure at a first fixed angle (e.g., an acute angle) and a second fixed bite ramp having a ramp structure at a second fixed angle (e.g., an obtuse angle, a different acute angle, or a right angle) that is different from the first fixed angle. Kits may include two or more bite ramps, each with different angles, or some having a first angle and others having one or more other angles. In addition, the bite ramps included in the kit may include ramp elements of different lengths (e.g., longer lengths may be useful for treating more severe class II malocclusions).

FIGS. 5-8 illustrate exemplary kits comprising a plurality of bite ramps. Each bite ramp includes a tooth-attachment element, a ramp element attached to the tooth-attachment element so as to provide a ramp structure at a pre-selected angle for engagement with a corresponding tooth of the opposite dental arch upon closing the patient's mouth. In the case of adjustable bite ramps, the kit may also include means for locking the ramp element at a fixed angle relative to the tooth-attachment element.

Figure 5:
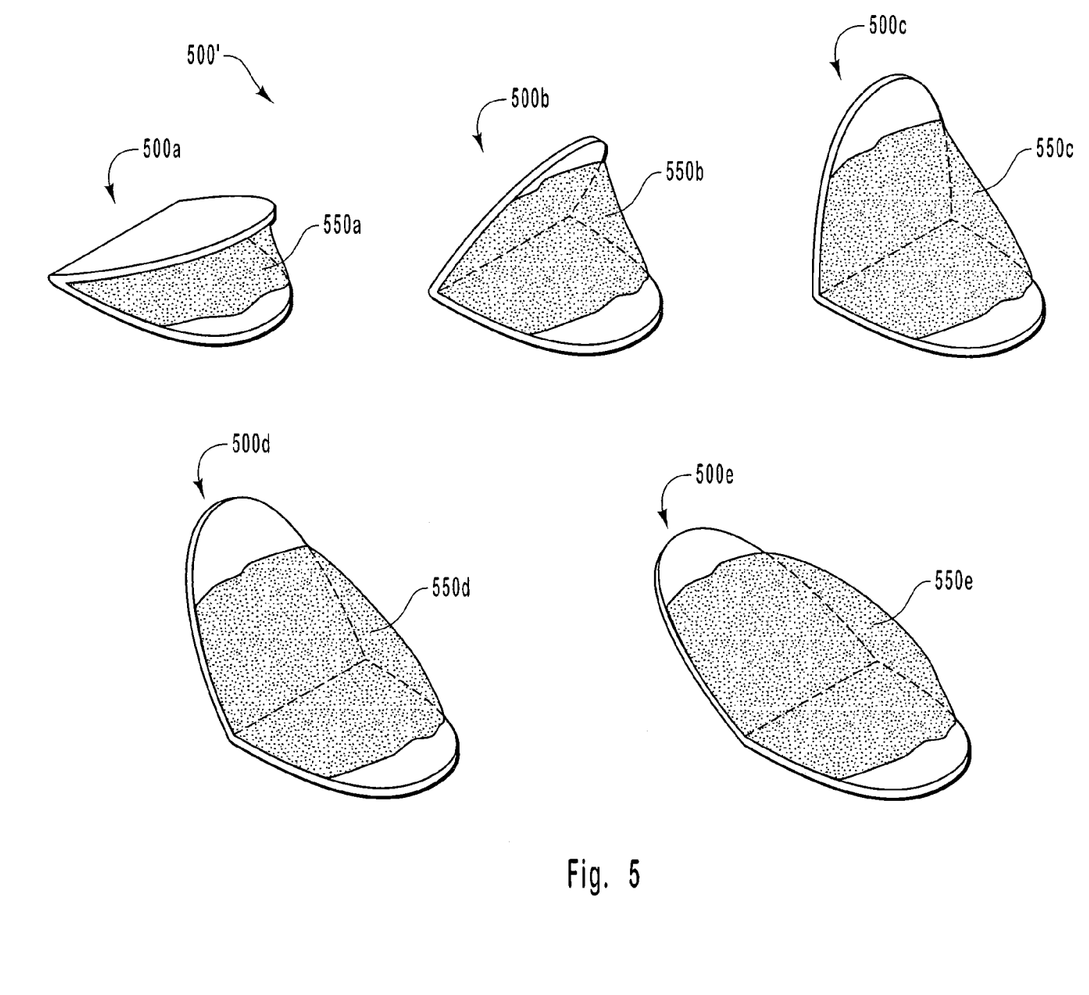
FIGS. 5-8 depict alternative exemplary kits including a plurality of bite ramps having different pre-selected angles.

The kit 500' of FIG. 5 includes bite ramps 500a, 500b, 500c, 500d, and 500e having predetermined angles of 30°, 60°, 90°, 120°, and 150°, respectively. Although each bite ramp is illustrated with different predetermined angles, the kit may include ramps having any desired angle (e.g., two or more having the same angle). Each bite ramp within kit 500' includes means for locking the ramp element at a fixed angle relative to the tooth attachment element. In the embodiment illustrated in FIG. 5, the locking means comprises a curable resin (550*a*, 550*b*, 550*c*, 550*d*, and 550*e*, respectively) between the tooth attachment element and the ramp element. A curable resin is one example of means for locking the ramp element at a fixed angle relative to the tooth-attachment element. The curable resin may be placed and cured during manufacture, or else it may be placed and cured by a dental practitioner during placement onto a person's teeth so placement and curing of the resin during installation allows for desired adjustment to one or more of the bite ramps.

Figure 6:
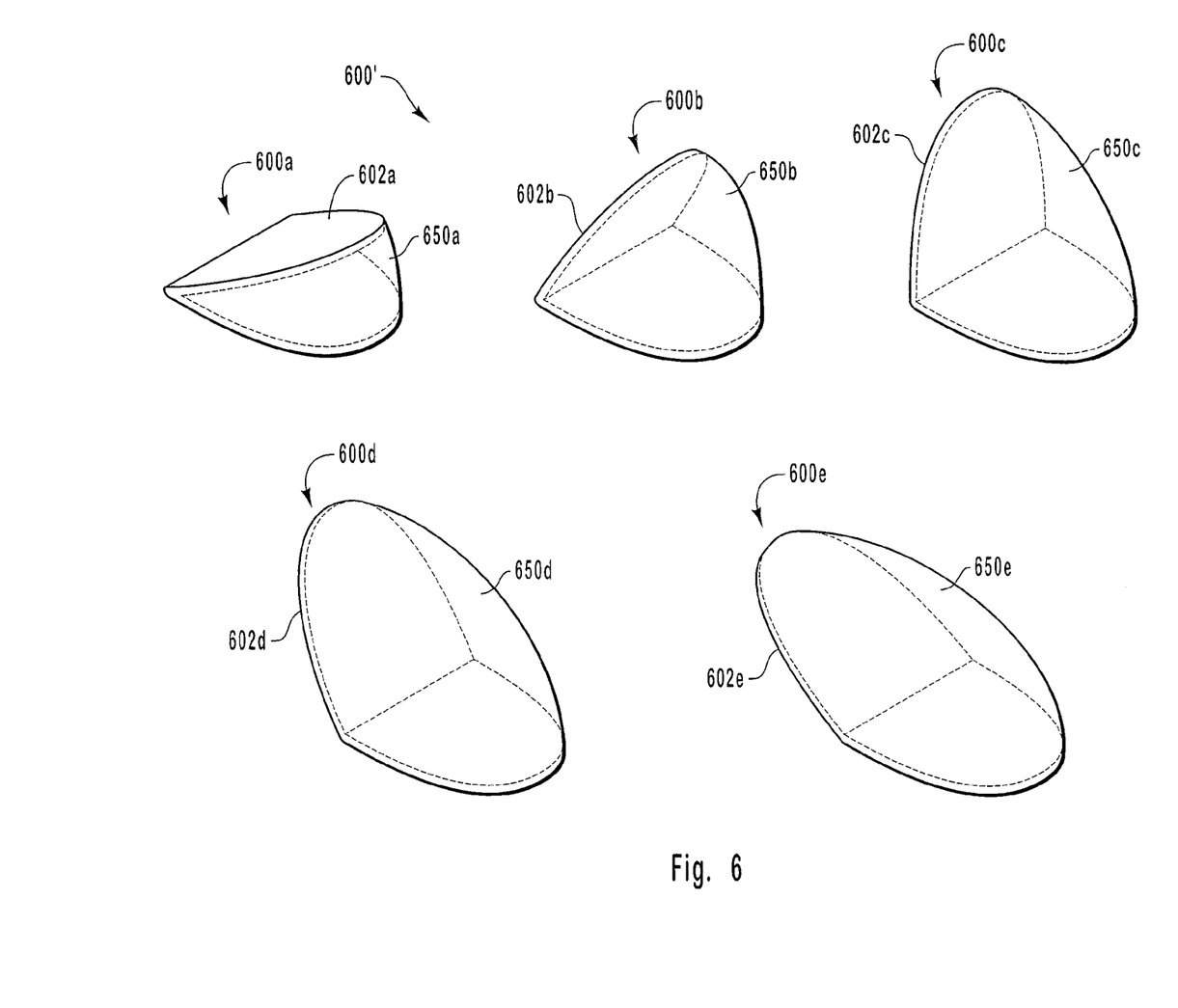

FIG. 6 illustrates an alternative kit 600' including bite ramps 600*a*, 600*b*, 600*c*, 600*d*, and 600*e* having predetermined angles of 30°, 60°, 90°, 120°, and 150°, respectively. Although each bite ramp is illustrated with different predetermined angles, the kit may include ramps having any desired fixed angle (e.g. two or more having the same angle). Each bite ramp within kit 600' includes means for locking the ramp element at a fixed angle relative to the tooth attachment element. In the embodiment illustrated in FIG. 6, the locking means comprises a shoe fitted and attached between the ramp element and tooth attachment element of each bite ramp. Each shoe (650*a*, 650*b*, 650*c*, 650*d*, and 650*e* respectively) is configured to form a flush fit against the tooth-attachment structure ((602*a*, 602*b*, 602*c*, 602*d*, and 602*e* respectively) of each bite ramp. Similar to the shoes illustrated and described with respect to FIGS. 3A-4B, each shoe (650*a*, 650*b*, 650*c*, 650*d*, and 650*e*) includes a planar lower surface for engagement with a person's corresponding tooth of the opposite dental arch, and a rounded upper surface. The shoes are an alternative example of means for locking the ramp element at a fixed angle relative to the tooth attachment element. They may be pre-installed or installed during placement or use of the bite ramps.

Figure 7:
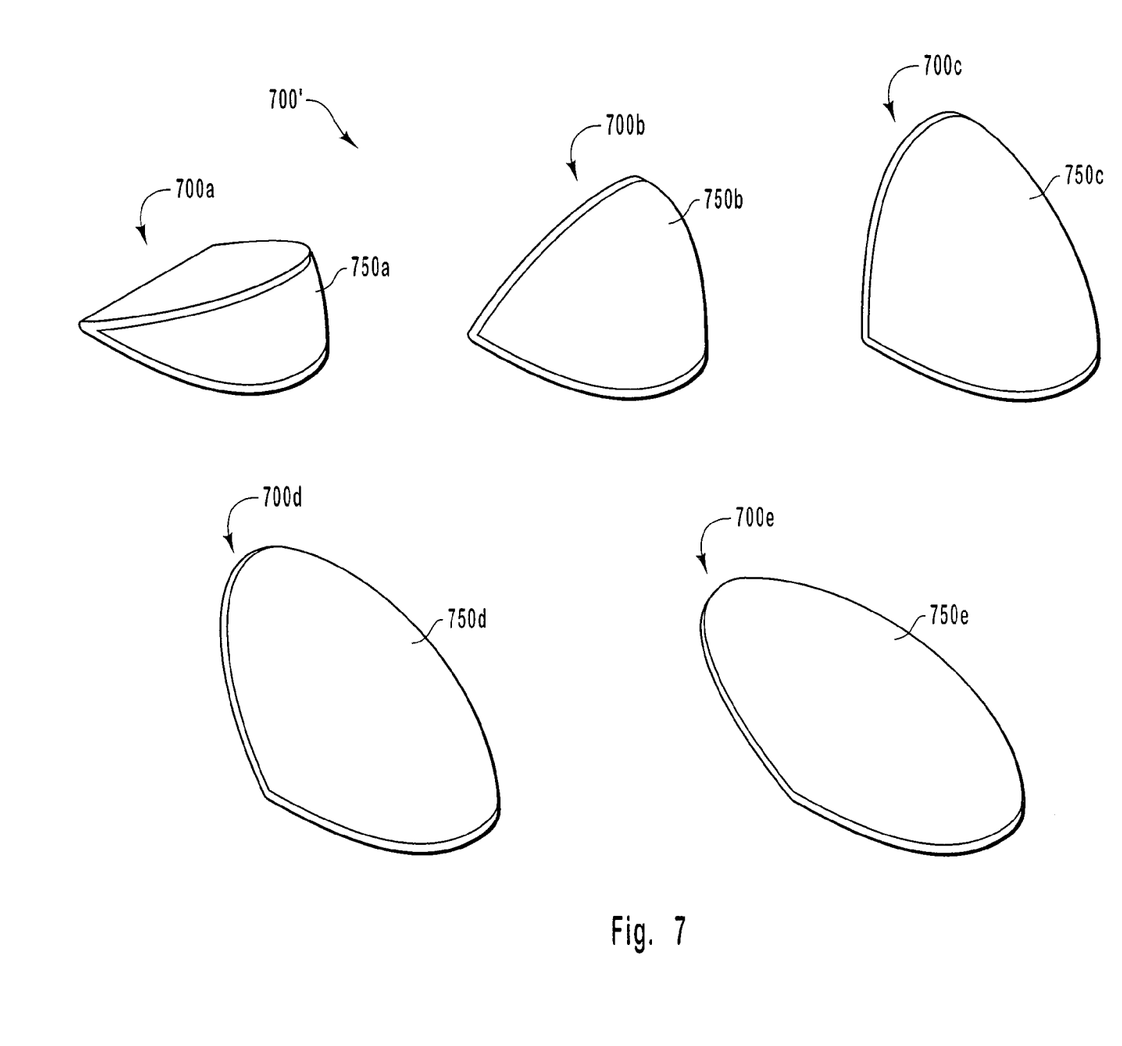

FIG. 7 illustrates an alternative kit 700' including fixed bite ramps 700*a*, 700*b*, 700*c*, 700*d*, and 700*e* having fixed predetermined angles of 30°, 60°, 90°, 120°, and 150°, respectively. Although illustrated with different predetermined angles, the kit may include ramps having any desired angle (e.g. two or more may have the same angle). Each fixed bite ramp within kit 700' includes means for locking the ramp element at a fixed angle relative to the tooth attachment element. In the embodiment illustrated in FIG. 7, the locking means comprises a fixed wedge (750*a*, 750*b*, 750*c*, 750*d*, and 750*e* respectively) attached or formed between the ramp element and tooth attachment element of each bite ramp. The fixed wedges may be formed from the same or a different material than the tooth-attachment element and the ramp element. According to one embodiment, the fixed wedge, the tooth-attachment element, and the ramp element may be formed as a single piece (e.g., through injection molding a plastic). The fixed wedges are an alternative example of means for locking the ramp element at a fixed angle relative to the tooth attachment element.

Figure 8:
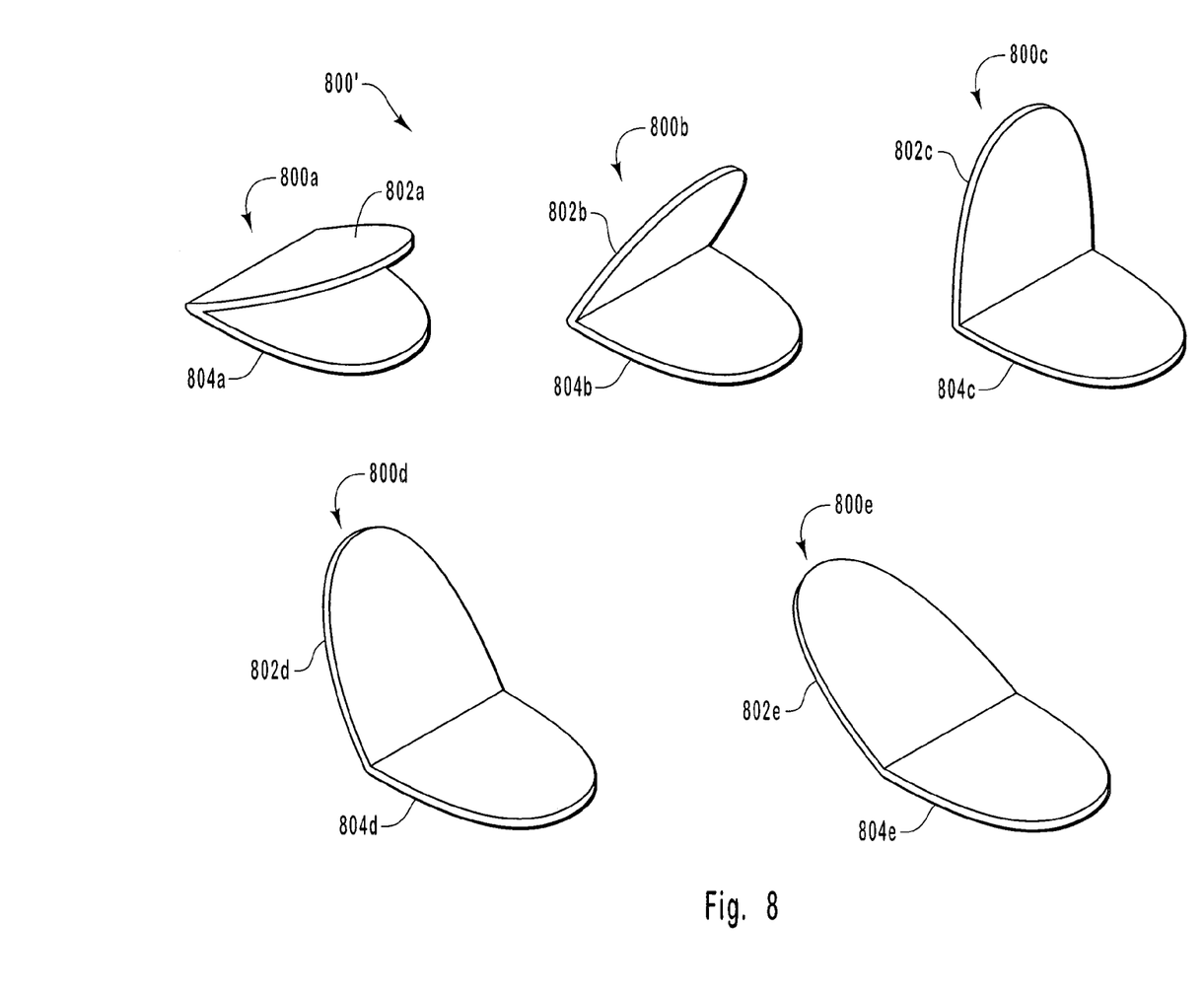

FIG. 8 illustrates an alternative kit 800' including bite ramps 800*a*, 800*b*, 800*c*, 800*d*, and 800*e* having predetermined angles of 30°, 60°, 90°, 120°, and 150°, respectively. Although illustrated with different angles, the kit may include ramps having any desired angle. In one embodiment, the bite ramps in kit 800' are adjustable. In another embodiment, the bite ramps are substantially fixed by virtue of the thickness and/or material rigidity of the bite ramps. Thus, the locking means may comprise the thickness and/or material selected for the tooth-attachment element and the ramp element. For example, the fixed angle between the ramp element (804*a*, 804*b*, 804*c*, 804*d*, and 804*e* respectively) and the tooth-attachment element (802*a*, 802*b*, 802*c*, 802*d*, and 802*e* respectively) may be established by forming the ramp element and tooth-attachment element from a rigid material having a desired thickness sufficient to substantially maintain the ramp element at a fixed angle relative to the tooth attachment-element. The rigidity and thickness of the material maintains the fixed angle during orthodontic use. The rigidity and thickness of the material of the tooth-attachment element and the ramp element is an alternative example of means for locking the ramp element at a fixed angle relative to the tooth attachment element.

Although kits 500', 600', 700', and 800' have been described and illustrated as including five bite ramps at different angles, it is to be understood that the inventive kits may include two or more bite ramps, and may include any combination of ramp angles. Kits of bite ramps having ramps at various pre-selected angles allow an orthodontic practitioner to choose a bite ramp or ramps having a desired angle configured to move the lower jaw forward, backward, or not at all, depending on the angle(s) selected.

It is to be understood that any of the bite ramps disclosed herein can be configured and used to move the lower jaw forward or backward, or not at all, depending on the final configuration of the adjustable bite ramp(s).

The present invention may be embodied in other specific forms without departing from its spirit or essential characteristics. For example, it may be desirable to use the adjustable bite ramps in treating medical joint problems. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A kit for use in an orthodontic treatment, comprising:
   a plurality of fixed bite ramps, each comprising:
      a first portion that is generally a flat, planar surface that is sized and shaped so as to generally conform to the lingual area of a person's front tooth so as to be configured as a tooth-attachment element for bonding entirely behind a person's front tooth to the lingual surface of a person's front tooth; and
      a second portion extending as an integral part of the first portion, the second portion being a generally flat, planar surface that essentially mirrors in size and shape the first planar surface but is bent relative to the first planar surface along a common bend line, the second planar surface of the bite ramp being configured so that it is bent at a fixed angle relative to said first planar surface configured as a tooth-attachment element so that the second planar surface is adapted for engagement with a corresponding tooth of the opposite dental arch upon closing the patient's mouth; and
   the plurality of bite ramps including at least a first bite ramp having a ramp at a first angle and a second bite ramp having a ramp at a second angle, said second angle being different from said first angle; and
   a curable resin comprising an adhesive resin for adhesively attaching at least one said bite ramp to a patient's teeth during use.

2. A method of using a kit of bite ramps comprising:
   providing a kit of bite ramps as recited in claim 1:
   selecting one or more bite ramps having a desired ramp angle for engagement with the corresponding tooth of the opposite dental arch upon closing the patient's mouth; and attaching said tooth-attachment element of said selected one or more bite ramps to the lingual surface of one of a patient's teeth.

3. A method as recited in claim 2, wherein said bite ramps are fixed to the lingual surface of the upper incisors.

4. A method as recited in claim 2, further comprising using at least one elastic to effect a desired movement of the lower jaw.

5. A kit as recited in claim 1, at least one of said first and second angles being an acute angle.

6. A kit as recited in claim 1, at least one of said first and second angles being an obtuse angle.

7. A kit as recited in claim 1, at least two of the bite ramps having bite ramps at right angles.

8. A kit as recited in claim 1, further comprising means for locking said ramp elements of at least a first and a second bite ramp in the kit, so that a first bite ramp has a first fixed angle relative to its tooth-attachment element, and a second bite ramp has a second fixed angle relative to its tooth-attachment element.

9. A kit as recited in claim 8, wherein said means for locking said ramp elements comprises a curable composition for placement between each said tooth-attachment element and its corresponding ramp element.

10. A kit as recited in claim 8, wherein said means for locking said ramp elements comprises a fixed wedge attached or formed between each said tooth-attachment element and its corresponding ramp element.

11. A kit as recited in claim 10, wherein said fixed wedge, said tooth attachment element, and said ramp element are formed as a single piece for the each of the first and second ramps.

12. A kit as recited in claim 8, wherein said means for locking said ramp element comprises the rigidity and/or thickness of the material of each said tooth-attachment element and its corresponding ramp element.

13. A kit as recited in claim 8, wherein said means for locking said ramp element comprises a shoe fitted and attached between each said tooth-attachment element and its corresponding ramp element, said shoe having a substantially planar lower surface for engagement with a person's corresponding tooth of the opposite dental arch, and a rounded upper surface.

* * * * *